United States Patent [19]

Seidel et al.

[11] Patent Number: 5,445,820
[45] Date of Patent: Aug. 29, 1995

[54] STREPTOLYSIN O PEPTIDE ANTIGENS AND METHODS FOR THE DETERMINATION OF STREPTOLYSIN ANTIBODIES

[75] Inventors: Christoph Seidel, Weilheim; Geoffrey Burns, Munich; Wolf-Dieter Engel, Feldafing, all of Germany

[73] Assignee: Boehringer Mannheim GmbH, Mannheim, Germany

[21] Appl. No.: 158,351

[22] Filed: Nov. 29, 1993

[30] Foreign Application Priority Data

Nov. 28, 1992 [DE] Germany ............... 42 40 056.2

[51] Int. Cl.6 .............. A61K 39/02; A61K 39/09; A61K 37/02; C07K 7/00; C07K 17/00
[52] U.S. Cl. .............. 424/237.1; 424/234.1; 424/244.1; 530/300; 530/327; 530/328; 435/7.34
[58] Field of Search .............. 530/300; 424/92

[56] References Cited

U.S. PATENT DOCUMENTS 4,021,541  5/1977  Lange et al. .............. 424/92
5,258,504  11/1993 Althaus et al. .............. 530/417
5,354,846  10/1994 Kehoe .............. 530/350

FOREIGN PATENT DOCUMENTS 0369825  5/1990  European Pat. Off. .
2226563  7/1990  United Kingdom ........ C12N 15/00
2233977A 1/1991  United Kingdom .

OTHER PUBLICATIONS

Kehoe et al., "Nucleotide Sequence of the Streptolysin O (SLO) Gene: Structural Homologies between SLO and Other Membrane-Damaging, Thiol-Activated Toxins", *Infection and Immunity*, vol. 55, No. 12, Dec., 1987, pp. 3228-3232.
Database Summary of JP-A-1 290 698, Nov. 1989.

*Primary Examiner*—Christine M. Nucker
*Assistant Examiner*—Nita M. Minnifield
*Attorney, Agent, or Firm*—Nikaido, Marmelstein, Murray & Oram

[57] ABSTRACT

SLO peptide antigens are described. These peptide antigens are suitable for the determination of SLO antibodies, as immunogens for the production of antibodies against SLO.

7 Claims, No Drawings

STREPTOLYSIN O PEPTIDE ANTIGENS AND METHODS FOR THE DETERMINATION OF STREPTOLYSIN ANTIBODIES

The invention concerns streptolysin peptide antigens, a process for the production of these peptide antigens as well as a method for the determination of streptolysin antibodies using the peptide antigens.

Streptolysin O (SLO) is a protein from streptococci which causes cell lysis by forming tunnel structures in the cell membrane, Streptolysin O is a toxin which can be activated by thiol and represents an important parameter for testing bacterial virulence. Antibodies against streptolysin are observed in the blood after an infection by streptococci. Consequently it should be possible to detect a streptococcal infection by an immunological test in which peptides are used which bind with high affinity to such antibodies and which can be used to reliably detect these antibodies, The DNA and amino acid sequence of streptolysin O is known from M. A. Kehoe, Infection and Immunity 55 (1987), 3228–3232. Streptolysin O is composed of 571 amino acids and has a molecular weight of 63645 D. Streptolysin O has a 33 amino acid long signal peptide at the N-terminus which is cleaved off when SLO is secreted to form a mature peptide of 538 amino acids in length and with a molecular weight of 60151 D. In addition on the basis of in vitro experiments it is assumed that native SLO is proteolytically cleaved during which a fragment with a molecular weight of 7000 D is additionally cleaved off. The amino acid sequence of the N-terminal part of SLO which is cleaved off during secretion has not yet been determined by sequence analysis but has been ascertained on the basis of the nucleotide sequence. The reason for this is that this N-terminal fragment is presumably present in extremely low amounts in body fluids such as for example in blood.

The determination of antibodies against streptolysin O (group A) is used in the diagnosis of streptococcal infections which for example cause joint rheumatism and glomerulonephritis. This so-called ASLO test is particularly useful for the differential diagnosis of joint rheumatism and rheumatism.

The detection of streptolysin O is at present usually carried out by haemolysis tests (for example using sheep erythrocytes) or by latex agglutination tests (J. Clin. Microbiol. 26 (1988) 1406–1408) which are very time-consuming and cannot be automated.

The object of the present invention is therefore to provide antigens which are specific for anti-streptolysin O antibodies and are suitable for simple immunological tests for anti-streptolysin antibodies.

The object is achieved by streptolysin O peptide antigens which have a negative band at 190–200 nm in the CD spectrum and contain at least one of the amino acid sequences SEQ ID NO: 1 PKPESSELTTE
SEQ ID NO: 2 QKTDDMLNSNDMI
SEQ ID NO: 3 IKLAPKEMPLE
SEQ ID NO: 4 EMPLESAEKEEKK
SEQ ID NO: 5 YDDKGKEVITK or partial sequences thereof of at least 4 amino acids in length.

It is important for the suitability of the peptide antigens according to the invention that they are not present in a defined folded structure but are linear. Such a linear structure is also denoted "random coil" structure. CD spectroscopy can be used to examine whether an oligopeptide has such a structure. A peptide with random coil structure has a negative band in the CD spectrum between 190 and 200 nm (cf. Ann. Rev. Biophys. Chem. 17 (1988) 145–166).

It has been demonstrated that the peptide SEQ ID NO: 2 or 5 or the peptide combination SEQ ID NO: 1, 3 and 4 enable a specific detection of anti-SLO antibodies. The sensitivity can be increased further by combination with the other peptide antigens according to the invention.

Preferred combinations (mixtures) are

SEQ ID NO: 2, 5
SEQ ID NO: 1, 2, 3, 4
SEQ ID NO: 1, 2, 3, 4, 5
SEQ ID NO: 1, 3, 4, 5

The underlined partial sequences shown above are preferably used. Partial sequences with a maximum length of 7 amino acids or 4–7 amino acids in mixtures are particularly preferably used. It is expedient to determine streptolysin antibodies by immunological tests in which antibodies against streptolysin are detected in body fluids. Binding partners for anti-streptolysin antibodies are therefore required for such immunological tests.

An anti-SLO antibody test is carried out according to methods familiar to a person skilled in the art. The invention therefore also concerns a method for the determination of SLO antibodies which is characterized in that the sample is incubated with the peptide antigens or partial sequences thereof with at least 4, preferably 4–7, amino acids of SEQ ID NO: 2 and/or 5 or with the peptide combination SEQ ID NO: 1, 3 and 4 and the amount of anti-SLO antibodies bound to the peptide antigen is determined under conditions which enable the formation of an antibody-antigen complex. The underlined partial sequences are preferably used.

A combination of SEQ ID NO: 2 and/or 5 or partial sequences thereof with at least one peptide antigen of SEQ ID NO: 1, 3 and 4 is preferably used.

It is also preferred that sequences SEQ ID NO: 1–5 or partial sequences thereof be combined with any desired amino acids to form a synthetic oligopeptide and to use this according to the invention. In doing so, it is merely necessary to ensure that the antigen retains a random coil structure.

The peptide antigens can for example be combined by using several individual peptide antigens or by covalently linking the peptide antigens together, appropriately via an amino acid bridge that can also differ from sequences of amino acids which occur naturally in SLO proteins or can represent a peptide linker.

The peptide antigens ID NO: 2 or 5 are used alone in concentrations of preferably 0.2–1 µg/ml.

In combinations, the peptide antigens are preferably used in an amount of 0.01–1 µg/ml, particularly preferably in the following amounts:

| peptide antigen | Amount in the combination (µg/ml) range | particularly preferred range |
| --- | --- | --- |
| 1 | 0.02–1.50 | 0.20–0.50 |
| 2 | 0.01–0.50 | 0.05–0.20 |
| 3 | 0.05–2.50 | 0.50–0.80 |
| 4 | 0.02–1.50 | 0.20–0.50 |
| 5 | 0.01–0.50 | 0.05–0.20 |

Heterogeneous and homogeneous immunoassays are used for the detection. The heterogeneous tests allow washing steps which considerably reduce the measured signal background and can as a result considerably increase the sensitivity.

The determination can for example be carried out by a radioimmunoassay, enzyme-immunoassay or by immunofluorescence. The peptide antigen is usually immobilized for this. The sample which is to be examined for anti-SLO antibodies is added and the antibodies bound to the antigen are determined via a labelled anti-human immunoglobulin antibody. The peptide antigen according to the invention can be immobilized adsorptively, covalently or by means of a biological binding pair such as biotin/streptavidin, antibody/antigen or sugar/lectin. In this case the peptide antigen is bound covalently to one of the partners.

The peptide antigens according to the invention can be immobilized for immunoassays preferably according to methods familiar to a person skilled in the art for example on beads, plastic tubes or microtitre plates (preferably made of polystyrene or copolymers of polystyrene). This is preferably carried out by non-specifically adsorbing the peptide antigen onto the surface or by binding it covalently to surfaces with functional groups or to activated surfaces. The non-specific adsorption can be improved by linking the peptide antigen to a protein to form a conjugate and to use this conjugate for the adsorption (cf. e.g. EP-A 0 269 092). It can also be bound via an immobilized antibody. In this case, care should be taken that the binding of the antibody or protein to the peptide antigen does not block the epitope.

The conjugation of the peptide antigen to the binding partner is preferably achieved by means of a spacer. It is expedient that this spacer contains 10–50, preferably 10–30, atoms and it is also preferably a substantially linear molecule. Examples of this are spacers composed of alkyl, polyether or polyamide chains. In a particularly preferred embodiment, a peptide antigen of 4–9 amino acids in length is bound via a linear spacer of 10–30 atoms to the carrier. If it is intended to use a spacer made of amino acids, then it is expedient that this be composed of amino acids which do not correspond to the sequence in the immediate vicinity of the peptide antigen in the SLO gene.

In a preferred embodiment the peptide antigen according to the invention is bound covalently to biotin and immobilized by means of an avidin/streptavidin solid phase.

Determination methods are also suitable in which the detection is not by means of a labelled antibody but of a labelled further peptide antigen of SEQ ID NO: 1–5 or partial sequences thereof.

A further particularly advantageous embodiment of the assay using these peptides is an immunoassay in which coated particles are used (LPIA). In this system particles which are coated with individual peptides or a mixture of peptides are mixed with the sample. The particles are agglutinated in the presence of antibodies directed towards SLO. The degree of agglutination can be measured qualitatively with the naked eye or quantitatively with the aid of a photometer, nephelometer or another suitable measuring instrument.

Various particles can be used. The use of latex particles is particularly preferred. However, a number of other particles can be used including for example metal sols (e.g. gold sols), liposomes or polystreptavidin.

The particles (preferably latex particles) can be coated with antibodies and antigens according to methods familiar to a person skilled in the art. They are usually coated either by adsorption or covalent binding. However, it is also possible to use biological binding pairs. The use of biotinylated peptides which can be applied to avidin/streptavidin latex particles is particularly advantageous.

It is advantageous that the the latices are coated with antigens via a spacer. Suitable spacers are described above.

A further advantageous embodiment of the immunoassay to detect anti-SLO antibodies using these peptides is the FPIA, EMIT or CEDIA technique.

In the fluorescence polarization immunoassay (FPIA), the peptide antigen according to the invention is labelled with a fluorescent substance. These molecules absorb light energy and release it in a period of about $10^{-8}$ sec as light of a longer wavelength. If the fluorophore is excited by polarized light, then the degree of polarization of the emitted light is dependent on the speed of rotation of the tracer (peptide antigen-fluorophore conjugate). Binding of the tracer to an antibody hinders the rotation of the fluorophore. The free tracer rotates more rapidly and depolarizes the excitatory light more than the larger, more inert antibody-tracer complex. The more anti-SLO antibodies are present in the sample, the more antibody-tracer complexes are formed and the more fluorescence polarization can be measured (W. Dandliker et al., Journal of Exp. Med. 122 (1965), 1029).

In the enzyme multiplied immunoassay technique (EMIT), the peptide antigen is coupled covalently to the marker enzyme in such a way that the enzymatic activity is retained. However, after an anti-SLO antibody binds to the peptide antigen moiety, the substrate binding to the enzyme is sterically hindered so that the enzyme cannot react with the substrate. The enzymatic activity is thus inversely proportional to the concentration of the anti-SLO antibody to be analysed in the sample solution (Gunzer et al., "Kontakte III, 1980, 3–11 and K. Rubenstein, Biochemical and Biophysical Research Communications 47 (1972), 846–851).

In the CEDIA technique (Henderson et al., Clinical Chemistry 32 (1986), 1637–1641), the test utilizes particular enzymes, such as for example $\beta$-galactosidase which are present as two components each of which is enzymatically inactive, i.e. a large polypeptide (enzyme acceptor) and a small polypeptide (enzyme donor), and these components associate spontaneously to form an enzymatically active protein. The peptide antigen is bound to the enzyme donor in such a way that the association of the enzyme donor with the enzyme acceptor to form the active enzyme is not impeded by this binding. This association is, however, inhibited when an antibody against the peptide antigen binds to the peptide antigen-enzyme donor complex. Thus active enzyme can be formed in a reagent solution in which the enzyme acceptor and peptide antigen-enzyme donor complex are present and enzymatic activity is measured. After addition of the sample solution, the anti-SLO antibody from this sample solution binds to the peptide antigen-enzyme donor complex and thus prevents the formation of the active enzyme. The measured signal is thus inversely proportional to the amount of antibody present.

The peptide antigens according to the invention can be produced according to methods for peptide synthesis familiar to a person skilled in the art. The invention therefore in addition concerns a process for the production of the peptide antigen according to the invention, wherein the amino acid forming the C-terminal end is bound to a support, the peptide antigen according to the invention is synthesized stepwise starting at the C-terminal end and this is subsequently cleaved from the support.

Details of this are that an amino acid is linked, for example via its carboxyl group, to an insoluble polymer that can be easily filtered and then the peptide chain is synthesized stepwise starting at the C-terminal end. For this purpose a N-protected amino acid is reacted with a reactive group of the artificial resin. The Nα protecting group is removed from the amino acid anchored covalently to the carrier particle and the resulting amino acyl polymer is reacted with the next N-protected amino acid. All excess reagents and by-products are removed by simple filtration. Once the desired peptide sequence has been produced in this manner, the covalent binding between the C-terminal amino acid and the anchor group of the polymer support is cleaved. The insoluble support is removed by simple filtration from the peptide which is now located in the solution. The peptide is purified by means of chromatographic methods.

The peptide antigens according to the invention can for example be produced according to Merrifield, JACS 85 (1964) 2146. If a biotinylation is required this can for example be carried out according to PNAS USA 80 (1983) 4045. A preferred biotinylation agent for this is biotinylaminocaproic acid-N-hydroxysuccinimide ester.

A preferred process for the production of biotinylated peptide antigens is to introduce a biotin residue at the N-terminus during a solid phase synthesis of the peptide antigen.

This process is preferably used when the peptide antigen contains several s-lysineamino groups which are not intended to be biotinylated. This is for example the case when N-α-Fmoc-N-ε-biotinyl-aminocaproyl-lysine, N-αFmoc-N-s-biotinyl-lysine or, for the biotinylation of the N-terminal amino acids, biotin, biotinylaminocaproic acid or dimethoxytritylbiotin are used with an activation reagent such as dicyclohexylcarbodiimide or as an active ester.

In a further preferred embodiment, a detection antibody which is for example directed towards the Fc part of human IgG is immobilized. A monoclonal antibody is preferably used for this. The peptide antigen is then located in the solution. The antibody (analyte) to be detected and also all other antibodies in the sample liquid are bound by wall antibodies. The bound antibody can then bind the analyte which can be protected using a suitable detection system e.g. competitively using a peptide antigen-enzyme conjugate.

It is also possible by using the peptide antigens according to the invention to obtain antibodies by immunization methods familiar to a person skilled in the art which can be used to detect the infectious particle itself in an immunological test.

The invention therefore in addition concerns a process for the production of antibodies which is characterized in that a mammal is immunized with a peptide according to the invention which if necessary is bound to a carrier and the antibodies are isolated by known methods e.g. from the serum or the spleen.

In a preferred embodiment B-lymphocytes of the immunized animals are fused with a suitable cell line in the presence of transforming agents, the cell line which produces the desired antibodies is cloned and cultured and the monoclonal antibodies are isolated from the cells or from the culture supernatant.

The anti-SLO antibodies produced in this manner can for example be used as test standards in immunoassays for the detection of anti-SLO antibodies. In addition the anti-SLO antibodies produced in this way can be used in an immunological test for the detection of the SLO antigen itself.

The invention therefore in addition concerns a method for the determination of SLO which is characterized in that the sample is incubated with an antibody according to the invention under conditions which allow an antigen-antibody complex to form and the amount of the antibody-antigen complex formed is determined.

The detection of the antibody-antigen complex formed can be carried out using all methods familiar to a person skilled in the art such as enzyme-immunoassay, radioimmunoassay, immunofluorescence such as FPIA, homogeneous immunoassays such as CEDIA or EMIT or turbidimetric and nephelometric methods of determination. In contrast to the FPIA, CEDIA and EMIT methods for the determination of anti-SLO antibodies as described above, competitive test variants of these methods as they are known to a person skilled in the art are utilized for the determination of SLO. Competitive tests are particularly preferred in which, in addition to the antibodies according to the invention the peptide antigens according to the invention are used as haptens or polyhaptens or components of the enzyme donor (CEDIA), tracers (FPIA) or marker enzyme (EMIT). Competitive turbidimetric methods of determination are particularly preferred. For this, individual or several peptide antigens according to the invention are coupled to a carrier and the complex obtained is used as a hapten in an agglutination test. The turbidity is then reduced by the analyte to be determined to an extent which is proportional to the amount of analyte. 30 to 40 peptide antigens are preferably coupled to each carrier molecule. Binding of the peptide antigen according to the invention to the carrier can in this case be carried out directly via covalent bonds or indirectly by for example biotinylating the peptide antigen and coating the carrier material with streptavidin. Carrier molecules which are preferably used for this are proteins such as immunoglobulins, albumin, β-galactosidase, polymers such as aminodextrans or polylysines or particles such as latex or gold, in each case either alone or in combination with one another. Coupling to the carrier molecule is achieved in a known manner, for example using reagents such as glutaraldehyde, ethyldimethylaminopropylcarbodiimide, maleimidohexanoic acid-N-hydroxysuccinimide ester or other known homo or heterobifunctional linkers.

The peptide antigens according to the invention can be used as a standard in immunological tests for the quantitative determination of SLO. The invention therefore in addition concerns the use of the peptide antigens according to the invention as a standard in an immunological test for the determination of SLO. In certain cases, such as for example in agglutination tests, it may be advantageous to bind several peptides according to the invention with the same or different sequences to a carrier molecule.

The invention also concerns a process for the production of vaccines using the peptide antigens according to the invention as well as a vaccine for treating streptococcal infections containing a peptide antigen having the sequences SEQ ID NO: 2 or 5 or the combination SEQ ID NO: 1, 3, 4 or partial sequences thereof, which if desired are bound to a carrier, in a pharmacologically effective dose and in a pharmaceutically acceptable formulation.

These vaccines can be produced according to known methods. However, it is preferable to firstly lyophilize the peptide antigens and subsequently suspend them, if desired with the addition of auxiliary substances.

Vaccination with the vaccine or vaccine combinations according to the invention can be carried out by methods familiar to a person skilled in the art such as intradermally, intramuscularly, intraperitoneally, intravenously, subcutaneously and intranasally.

The vaccine can for example be suspended in physiological saline for intramuscular or subcutaneous administration. For an intranasal or intraocular application, the vaccine can for example be applied in the form of a spray or an aqueous solution. For local, for example oral, administration it is often necessary to temporarily protect the immunogens against inactivation by for example proteolytic enzymes in the cavity of the mouth or in the stomach. Such a temporary protection can for example be effected by encapsulating the immunogens. This encapsulation can for example be achieved by coating with a protective agent (microencapsulation) or by embedding a multitude of immunogens according to the invention in a protective carrier (macroencapsulation).

The encapsulation material may be semipermeable or become semipermeable when introduced into the human or animal body. A biologically degradable substance is usually used as the carrier for the encapsulation.

The invention is elucidated further by the following examples and sequence protocols.

EXAMPLE 1

Synthesis of H-PESSELTTE-OH (NS5/1)

The peptide was synthesized by means of Fmoc (fluorenyloxycarbonyl) solid phase synthesis. The reactions were carried out on a Labortec (Switzerland) SP 640 peptide synthesizer. The coupling reactions for the Fmoc amino acid derivative were carried out with 1.2 equivalents dicyclohexylcarbodiimide and 1.1 equivalents N-hydroxybenzotriazole for 90 minutes. Dimethylformamide was used as the reaction medium. The Fmoc group was cleaved off in 10 and 20 minutes using 20% piperidine in DMF 4.0 equivalents of the following amino acid derivates were used: Pro, Ser (with tert. butyl protecting group), Thr (with tert. butyl protecting group), Glu (with tert. butyl ester protecting group) and Leu. The coupling result was checked using the Kaiser test (Anal. Biochemistry 34 (1970) 595), the loading of the resin was determined by means of UV absorbance of the fulvene group released after each piperidine cleavage. The peptide was synthesized on 5 g Wang resin (polystyrene/1% divinylbenzene) with a loading of 0.50 mmol/g (JACS 95 (1973) 1328). After the synthesis the degree of loading was still 0.43 mmol/g.

The peptide was released with 200 ml trifluoroacetic acid, 20 ml ethandithiol, 20 ml m-cresol and 10 ml water in 30 minutes at room temperature. The cleavage solution was concentrated several times with toluene, the peptide was then precipitated with diethyl ester.

In order to remove the scavengers and other small molecules, the crude material was purified over a Sephadex G10 column. After lyophilization 2.4 g material with a purity of 54% (RP-HPLC) was obtained. In order to achieve the final purity of >95%, 400 mg peptide was purified by means of a preparative RP-HPLC column (40 mm×250 mm) filled with C18 material (5 micrometers, 300 angstrom) and a water/trifluoroacetic acid, acetonitrile/trifluoroacetic acid gradient. 87 mg 97.2% (HPLC) white material was obtained after lyophilization. The identity of the material was checked by means of FAB-MS.

EXAMPLE 2

In order to biotinylate the peptide antigen from example 1, a mole equivalent was dissolved as concentrated as possible (the solubility depends on the amino acid sequence) in argon-saturated potassium phosphate buffer (0.1 mol/l, pH 8.0) and admixed with 3 equivalents D-biotinyl-ε-aminocaproic acid-N-hydroxysuccinimide ester dissolved in argon-saturated dimethylformamide (solution of 1 μmol reagent in 5 μl DMF).

The reaction mixture was stirred under argon for 2 hours at room temperature and is monitored continuously by means of analytical RP-HPLC. As soon as <5% starting material was present, the reaction mixture was applied directly to a preparative RP-HPLC column and the product material was purified by means of a 0.1% trifluoroacetic acid/water to 0.1% trifluoroacetic acid/acetonitrile gradient (gradient: 0% to 100% in 90 minutes). The product material was obtained by concentration and lyophilization of the product fractions. The yields were between 40% and 90%. The following analytical methods were used: HPLC, HPCE and TLC for the purity, FAB-MS (mole peak) and TLC using specific staining reagents (p-dimethylaminocinnamaldehyde for biotin) for the identity and the assay was determined by means of microanalysis (nitrogen).

EXAMPLE 3

SLO antibodies are determined in a two-step sandwich immunoassay. Reagents having the following composition are used for the test.

Reagent 1:

Combination of biotinylated peptide antigens or individual biotinylated antigens.

40 mmol/l phosphate buffer pH 7.0

0.9% by weight NaCl

10% by volume bovine serum albumin

Reagent 2:

20 mU/ml of a conjugate of polyclonal antibody against human immunoglobulin (sheep) and peroxidase 40 mmol/l phosphate buffer pH 7.0

0.05% by weight Tween® 20

0.2% bovine serum albumin 0.2% bovine IgG 1 ml reagent 1 and 10 μl sample are incubated for 1 hour at room temperature in a polystyrene tube coated with streptavidin (produced according to example 1 of EP-A 0 334 578). It is subsequently washed three times with tap water and incubated with 1 ml reagent 2 for 1 hour at room temperature. It is subsequently washed three times with tap water. 1 ml ABTS® (2,2-azino-di[3-ethyl-benzthiazoline sulfonate(6)]-diammonium salt, 1.9 mmol/l, in 100 mmol/l phosphate-citrate buffer pH 4.4 with 3.2 mmol/l sodium perborate) is added for the detection reaction. After 60 minutes the absorbance at 420 nm is measured photometrically. The results are shown in Table 1.

Legend for the Tables:

±: negative/positive (the cut off for a positive signal in an ELISA is defined as the mean absorbance at 420 nm plus 3 standard deviations of a group of 10 negative control sera. The samples were measured at a sample dilution of 1:100).

The following antigen concentrations were used:

a) as an individual antigen in the test

| Antigen | Amount [μg/ml] |
|---|---|
| 1 | 0.35 |
| 2 | 0.20 |
| 3 | 0.60 |
| 4 | 0.35 |
| 5 | 0.20 | b) in the combinations

| Antigen | Amount [μg/ml] in combination | | | | |
|---|---|---|---|---|---|
| | 1 | 2 | 3 | 4 | 5 |
| 1 + 2 + 3 + 4 + 5 | 0.20 | 0.10 | 0.40 | 0.20 | 0.10 |
| 2 + 5 | — | 0.20 | — | — | 0.20 |
| 1 + 2 + 4 + 5 | 0.20 | 0.10 | — | 0.20 | 0.10 |
| 1 + 3 + 4 | 0.25 | — | 0.50 | 0.25 | — |

TABLE I

| Serum | SEQ ID NO: | | | | |
|---|---|---|---|---|---|
| | 1 | 2 | 3 | 4 | 5 |
| 1 | + | + | + | + | + |
| 2 | + | + | + | + | + |
| 3 | + | + | − | + | + |
| 4 | + | + | − | + | + |
| 5 | + | + | − | + | + |
| 6 | − | + | + | − | + |
| 7 | + | + | + | +? | + |
| 8 | − | + | − | + | + |
| 9 | + | + | + | + | + |
| 10 | − | + | − | + | (+) |
| 11 | + | + | − | + | (+) |
| 12 | + | + | − | + | + |
| 13 | − | + | + | − | + |
| 14 | − | + | + | − | + |
| 15 | + | + | + | + | (+) |

We claim:

1. A streptolysin O peptide antigen comprising at least a part of one of the amino acid sequences selected from the group consisting of SEQ ID NO: 1, SEQ ID NO: 2, SEQ ID NO: 3, SEQ ID NO: 4 and SEQ ID NO: 5, wherein said part of the amino acid sequences is at least 4 amino acids in length and wherein said antigen has a negative band between 190 and 200 nm in the CD spectrum.

2. The streptolysin O peptide antigen according to claim 1, comprising at least a part of each of the amino acid sequences SEQ ID NO: 1, SEQ ID NO: 2, SEQ ID NO: 3 and SEQ ID NO: 4.

3. The streptolysin O peptide antigen according to claim 2, further comprising at least a part of SEQ ID NO: 5.

4. The streptolysin O peptide antigen according to claim 1, wherein said part of the amino acid sequence from SEQ ID NO: 1 is PESSELTTE, from SEQ ID NO: 2 is TDDMLNSND, from SEQ ID NO: 4 is PLESAEK and from SEQ ID NO: 5 is YDDK-GKEVI.

5. The antigen according to claim 1, wherein said amino acid sequences are covalently linked together.

6. A combination of streptolysin O peptide antigens comprising at least a part of one amino acid sequence selected from the group consisting of SEQ ID NO: 2 and SEQ ID NO: 5, wherein said part of the amino acid sequence is at least 4 amino acids in length.

7. The combination of streptolysin O peptide antigens according to claim 6, further comprising at least a part of one amino acid sequence selected from the group consisting of SEQ ID NO: 1, SEQ ID NO: 3 and SEQ ID NO: 4, wherein said part of the amino acid sequences is at least 4 amino acids in length.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 1:

```
Pro Lys Pro Glu Ser Ser Glu Leu Thr Thr Glu
 1               5                   1 0
```

( 2 ) INFORMATION FOR SEQ ID NO: 2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 2:

```
Gln Lys Thr Asp Asp Met Leu Asn Ser Asn Asp Met Ile
 1               5                   1 0
```

( 2 ) INFORMATION FOR SEQ ID NO: 3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide (x i) SEQUENCE DESCRIPTION: SEQ ID NO: 3:

Ile Lys Leu Ala Pro Lys Glu Met Pro Leu Glu
1               5                   10

(2) INFORMATION FOR SEQ ID NO: 4:

(i) SEQUENCE CHARACTERISTICS:
      (A) LENGTH: 13 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO: 4:

Glu Met Pro Leu Glu Ser Ala Glu Lys Glu Glu Lys Lys
1               5                   10

(2) INFORMATION FOR SEQ ID NO: 5:

(i) SEQUENCE CHARACTERISTICS:
      (A) LENGTH: 11 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO: 5:

Tyr Asp Asp Lys Gly Lys Glu Val Ile Thr Lys
1               5                   10